United States Patent

Joung

[11] 4,304,008
[45] Dec. 8, 1981

[54] DONABLE SURGEON'S GLOVE FREE OF INNER SURFACE LUBRICATING POWDER AND METHOD OF MAKING SAME

[75] Inventor: John J. Joung, South Pasadena, Calif.

[73] Assignee: American Hospital Supply Corporation, Evanston, Ill.

[21] Appl. No.: 61,787

[22] Filed: Jul. 30, 1979

[51] Int. Cl.³ ............................................. A41D 19/00
[52] U.S. Cl. ...................................................... 2/167
[58] Field of Search .............. 2/167, 169, 168, 161 R, 2/161 A, 164, 159, 243 R; 428/447; 264/255, 306

[56] References Cited

U.S. PATENT DOCUMENTS

| | | | |
|---|---|---|---|
| Re. 24,953 | 3/1961 | Homeyer et al. | 428/447 X |
| 732,360 | 6/1903 | Lindsay | 2/168 |
| 2,668,789 | 2/1954 | Phreaner | 428/447 X |
| 2,781,288 | 2/1957 | Polmanteer | 428/447 |
| 2,789,933 | 4/1957 | Bargmeyer | 428/447 |
| 2,989,755 | 6/1961 | O'Brien et al. | 2/168 |
| 3,992,221 | 11/1976 | Homsy et al. | 2/168 X |

*Primary Examiner*—H. Hampton Hunter
*Attorney, Agent, or Firm*—Larry N. Barger; Donald L. Barbeau

[57] ABSTRACT

A powder free surgeon's glove of a material such as latex rubber, which has covalently bonded to its outer surface a halogen resistant layer, such as silicone. The inner surface of the glove has been halogen treated for smooth nontacky donning characteristics.

16 Claims, 4 Drawing Figures

DONABLE SURGEON'S GLOVE FREE OF INNER SURFACE LUBRICATING POWDER AND METHOD OF MAKING SAME

BACKGROUND

It is well-known that the highly stretchable latex surgeon's gloves are very difficult to don without a lubricating powder, such as cornstarch, etc. The use of such donning powder, while necessary in the commerical surgeon's gloves, is not desirable because it requires the surgeon to remove any excess powder after donning. If he does not do this, some of the lubricating powder can enter a surgical wound. Some reports believe that such powder could cause a granuloma in some instances.

Attempts to eliminate the donning powder have not been successful because the surgeons simply could not get the glove on. U.S. Pat. Nos. 3,845,031 and 3,992,221 describe a treatment for synthetic and natural rubber materials which include halogenating their surfaces. The former patent deals with providing a better "glueable" surface to rubber. The latter patent is attempting to provide a donable glove that does not require a lubricating powder. This proposal involves treating the glove with fluorine gas. Such fluorine treatment has a disadvantage of substantially weakening the rubber glove structure so that it cracks and breaks during stretching. This could be the reason why such glove has never been marketed.

SUMMARY OF THE INVENTION

The present invention overcomes the problem of the prior art by covalently bonding to an exterior surface of a highly stretchable surgeon's glove (such as of latex) an outer barrier glove of a halogen resistant material (such as silicone or urethane). The inner surface of the glove is then halogenated for easy donning without a powdered lubricant. Such glove is very sturdy and does not crack or delaminate when highly stretched in sharp angular condition in knuckle flexing and during donning.

THE DRAWINGS

DETAILED DESCRIPTION

Figure 1:
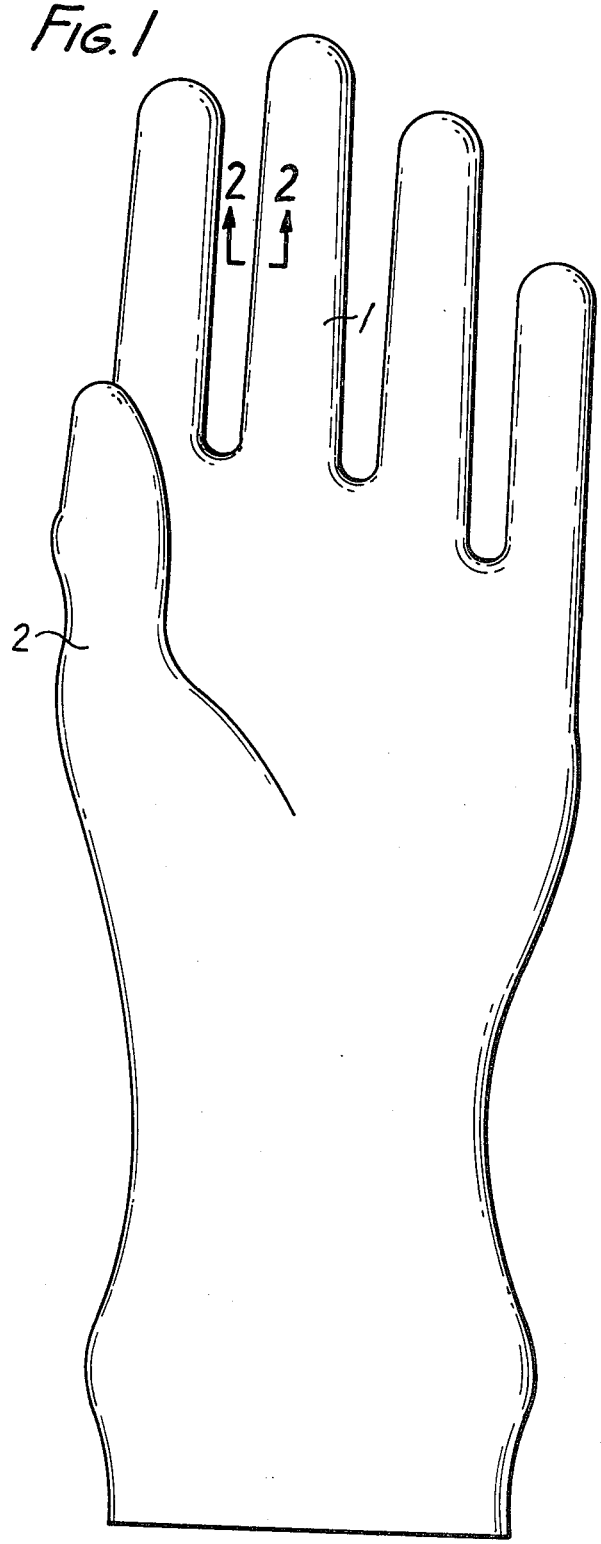
FIG. 1 is a front elevational view of the glove.
Figure 2:
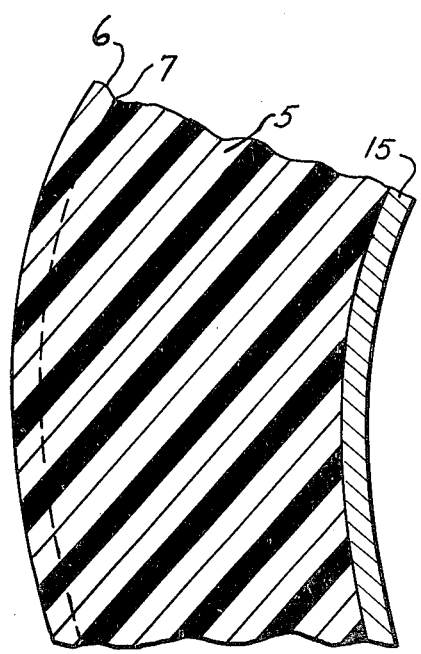
FIG. 2 is an enlarged fragmentary sectional view taken along line 2—2 of FIG. 1.

In FIG. 1, a surgeon's glove is shown with the typical finger area 1 and thumb area 2. The wall or shell forming the glove, as shown in FIG. 2, includes a support glove 5 which frequently is of a rubber latex material. An exterior backing glove 6 which preferably is of a silicone material is covalently bonded at an area 7 to the support glove 5. A halogenated area 15 forms the inner surface of the glove.

In a co-pending application entitled "Hypoallergenic Slip Resistant Gloves and Methods of Making Same," filed July 30, 1979, Ser. No. 61,788, a description is given for covalently bonding a silicone layer on an inner surface of the glove to prevent contact between a surgeon's hand and the rubber latex glove. Some surgeons, nurses, etc. are highly sensitive to certain components of natural rubber, such as sulphur and other accelerators and preservatives. The donning powder with the internal silicone boundary glove was reduced to about ⅓ of the normal amount, but was still required. The present patent application uses no donning powder on its inner surface, but cannot be considered hypoallergenic because materials from the latex glove can contact the hand of the surgeon or nurse when worn. The present glove is primarily for persons who are not ultrasensitive to materials in natural and synthetic rubber.

Applying the halogen resistant backing glove 6 to support glove 5 by means of covalent chemical bonds to prepare the glove for halogenation can be done as follows.

EXAMPLE 1

A ceramic glove form was preheated to 150° F. and through coagulant and latex dipping processes, as is well-known in the glove art, the latex glove of coagulum was deposited on the form. After air drying for 2-3 minutes, all soluble components in the coagulant, as well as in the latex, were dissolved in running water for 8 minutes. The dry coagulum on the glove form was cured at 260° F. for 20 minutes. The glove while still on the form was subjected to forced air cooling, until the temperature became 160° F.

The form was momentarily dipped into a priming solution composed of a sulfhydryl-alkylethoxysilane in isopropanol as disclosed in U.S. Pat. No. 3,434,869. The primed glove was then dipped in an RTV silicone coating and cured.

EXAMPLE 2

A similar procedure according to Example 1, except the primer and silicone are applied in a single step. In the present example, ½ liter of 3% 3-mercaptopropyl-triethyoxy-silane in isopropanol was added to 5 liters of 8% acetoxy-polydimethyl-siloxane in petroleum ether containing a small amount of fumed silica and the mixture stirred well. If desired, fumed silica could be eliminated. The unstripped gloves were dipped into the solution after they cooled to 150° F. When most of the solvent evaporated, the gloves were heated with steam at 210° F. for 5-20 minutes. The gloves were cooled in a cold air stream and then stripped from the form. The silicone layer was cured and did not delaminate or craze even when exhaustive repetitive stretching and releasing occured.

Figure 3:
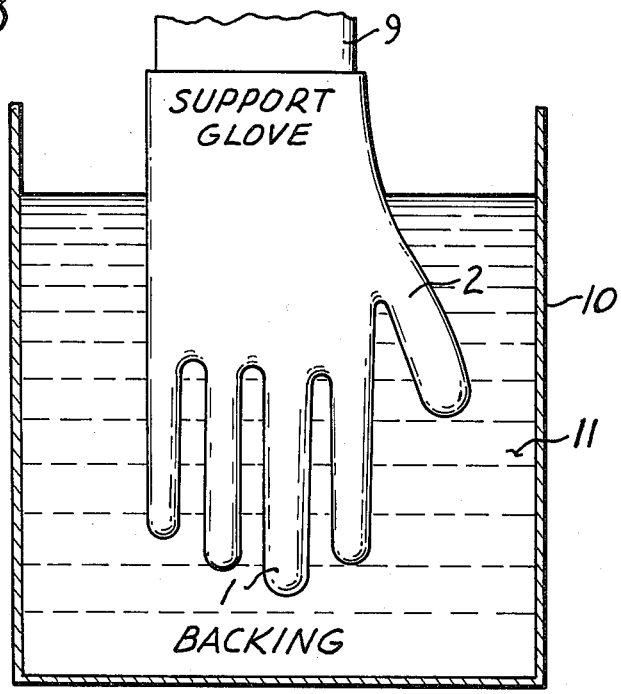
FIG. 3 is a schematic showing of the glove being dipped into a halogen resistant backing or barrier material to form the external backing glove.

The above process is schematically shown in FIG. 3 where the backing glove on a form 9 is dipped into a tank 10 containing the backing glove material 11, such as the silicone.

Figure 4:
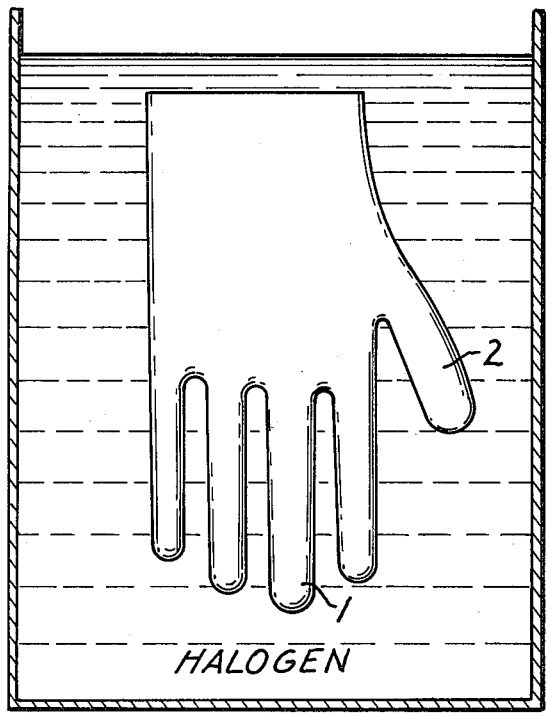
FIG. 4 is a schematic showing of the glove being halogenated after the backing glove has been applied.

The combined support glove (latex) and backing glove (silicone) which are covalently bonded together are then stripped from form 9 and halogenated as schematically shown in FIG. 4.

EXAMPLE 3

A surgeon's glove prepared according to Example 1 or 2 was stripped from the mold and halogenated in a 1% chlorine and 10% acetic acid in an aqueous solution for 5-20 minutes. The halogenated glove was then rinsed in 0.2% ammonia solution and dried. The dried gloves were finally heated to 70° C. for 10 minutes. The resulting glove was:

(1) easily donable without any lubricating powder;

(2) the silicone side was extremely smooth and had sufficient frictious properties to conveniently hold medical instruments whether wet or dry;

(3) the glove did not delaminate upon repeated stretching;

(4) halogenation did not affect or accelerate oxidation failure of the gloves, whereas unlaminated gloves could be cracked in several days even at a much lower degree of halogenation.

Other halogen sensitive elastomers for the support glove could be used, as well as other backing elastomers, so long as they met the general spirit of the present invention. For instance, synthetic as well as natural rubber latex could be used for the support glove to provide vinyl groups for covalent chemical bonding. Also, a polyurethane with an appropriate linker could be employed to provide a halogen resistant outer glove covalently bonded to the support glove.

The "powder free" donable glove works well when the support glove is of a natural latex rubber of 3-10 mil thickness. This glove can be manufactured by a process that does not use talc in its latex dipping slurry for mold release. Such process is described in a co-pending patent application entitled "Surgeon's Glove and Talc Free Process for Forming Same," filed July 30, 1979, Ser. No. 61,790. However, the present invention can work with conventional latex surgeon's gloves which include talc suspended in a dipping slurry when the gloves are dip coated to form the glove on a glove form. Regardless of the process for forming the latex support glove, it is preferably covalently bonded to the backing glove of silicone or polyurethane in which the backing glove has a thickness of from 0.25 to 2 mil.

In the foregoing description, specific examples have been used to describe the invention. It is understood by those skilled in the art that modifications can be made to these examples without departing from the spirit and scope of the invention.

I claim:

1. A powder-free surgeon's glove comprising: a support glove of a first elastomer having a halogenated inner surface and a backing glove of a second elastomer chemically secured to an outer surface of the support glove, wherein the second elastomer provides the glove with greater resistance to halogen degradation than does the first elastomer, whereby sharp angular flexing in the knuckle area as well as stretching and snapping during donning does not crack the laminated support glove nor delaminate it from this backing glove.

2. A surgeon's glove as set forth in claim 1, wherein the first elastomer is latex rubber.

3. A surgeon's glove as set forth in claim 1 wherein the second elastomer is silicone.

4. A surgeon's glove as set forth in claim 1, wherein the support glove has a thickness of 0.003 to 0.010 inch and the backing glove has a thickness of 0.0002 to 0.002 inch.

5. A surgeon's glove as set forth in claim 1, wherein the inner surface is chlorine halogenated.

6. A surgeon's glove as set forth in claim 1, wherein the backing glove has greater slip resistance than the support glove for manipulating surgical instruments.

7. A surgical glove as set forth in claim 1, wherein the second elastomer is capable of stretching as much or more than the first elastomer to prevent crazing in the knuckle area.

8. A method of making a powder-free surgeon's glove comprising the steps of:
    (a) forming a support glove of a first elastomer;
    (b) attaching a backing glove of a second elastomer to an exterior of the support glove, wherein the backing glove provides the glove with greater resistance to halogen degradation than does the support glove;
    (c) chemically bonding the two gloves together;
    (d) curing the backing glove; and
    (e) halogenating a surface of the support glove that is not protected by the backing glove to provide a surgeon's glove that is easily donnable without lubricating powders.

9. A method as set forth in claim 8, wherein the support glove is formed of latex rubber.

10. A method as set forth in claim 8, wherein the backing glove is formed of silicone.

11. A method as set forth in claim 8, wherein the support glove is halogenated with chlorine.

12. A method as set forth in claim 8, wherein the method includes the further step of heat treating the halogenated glove.

13. A method as set forth in claim 8, wherein the heat treating step is carried out at 50° to 110° C. for a period of 5 to 30 minutes.

14. A method as set forth in claim 8, wherein the halogenation step includes submerging the glove in an aqueous solution containing a halogen.

15. A method of improving the resistance of elastomeric gloves to halogen degradation, delamination, and cracking by chemically securing to the outer surface of said glove a second elastomeric glove of the type which provides greater resistance to halogen degradation than does the first elastomeric glove, and halogenating said glove.

16. The method of claim 15 wherein the elastomer of the second elastomeric glove is silicone.

* * * * *